(12) United States Patent
Joyner et al.

(10) Patent No.: US 12,097,312 B2
(45) Date of Patent: Sep. 24, 2024

(54) METHODS, SYSTEMS AND DEVICES FOR EXPRESSING BREASTMILK

(71) Applicant: Emory University, Atlanta, GA (US)

(72) Inventors: Andrea Braden Joyner, Decatur, GA (US); David Andrew Barr, Annahilt (GB)

(73) Assignee: Emory University, Atlanta, GA (US)

( * ) Notice: Subject to any disclaimer, the term of this patent is extended or adjusted under 35 U.S.C. 154(b) by 1011 days.

(21) Appl. No.: 16/971,581

(22) PCT Filed: Feb. 20, 2019

(86) PCT No.: PCT/US2019/018789
§ 371 (c)(1),
(2) Date: Aug. 20, 2020

(87) PCT Pub. No.: WO2019/164963
PCT Pub. Date: Aug. 29, 2019

(65) Prior Publication Data
US 2020/0397960 A1    Dec. 24, 2020

Related U.S. Application Data

(60) Provisional application No. 62/632,850, filed on Feb. 20, 2018.

(51) Int. Cl.
*A61M 1/06* (2006.01)
*A61M 1/00* (2006.01)

(52) U.S. Cl.
CPC .......... *A61M 1/06935* (2021.05); *A61M 1/06* (2013.01); *A61M 1/064* (2014.02);
(Continued)

(58) Field of Classification Search
CPC .... A61M 1/06; A61M 1/06395; A61M 1/064; A61M 2205/7536; A61M 2205/52
See application file for complete search history.

(56) References Cited

U.S. PATENT DOCUMENTS 5,954,690 A    9/1999  Larsson
6,440,100 B1   8/2002  Prentiss
(Continued)

FOREIGN PATENT DOCUMENTS

DE            382211 A1    11/1988

OTHER PUBLICATIONS

International Search Report and Written Opinion for PCT Application No. PCT/US2019/018789 dated Apr. 30, 2019.
(Continued)

*Primary Examiner* — Nathan R Price
*Assistant Examiner* — John A Doubrava
(74) *Attorney, Agent, or Firm* — Emory Patent Group

(57) ABSTRACT

The systems, methods, and devices can efficiently express breast milk while being visually and audibly discreet, and portable. The breastmilk expression system for extracting milk from a breast of a female may include an interface configured to deliver suction to a nipple of the breast. The system may include a breastmilk storage container configured to store breastmilk. The system may include a control device operatively coupled to the breastmilk storage container and the interface. The control device may include one or more pressure reservoirs configured to store negative pressure. The control device may be configured to cause passive suction at the interface to cause extraction of the breast milk by controlling delivery of the negative pressure stored in the one or more pressure reservoirs to the interface.

13 Claims, 6 Drawing Sheets

(52) U.S. Cl.
    CPC ............... *A61M 1/74* (2021.05); *A61M 1/067* (2021.05); *A61M 2205/3344* (2013.01); *A61M 2205/3584* (2013.01); *A61M 2205/52* (2013.01); *A61M 2205/7536* (2013.01); *A61M 2205/8206* (2013.01); *A61M 2209/088* (2013.01)

(56) References Cited

U.S. PATENT DOCUMENTS

| | | |
|---|---|---|
| 7,789,865 B2 | 9/2010 | Myers et al. |
| 8,118,772 B2 | 2/2012 | Dao et al. |
| 11,260,151 B2 | 3/2022 | O'Toole et al. |
| 2003/0191433 A1 | 10/2003 | Prentiss |
| 2003/0236491 A1 | 12/2003 | McKendry et al. |
| 2004/0133151 A1 | 7/2004 | Watanabe |
| 2004/0243105 A1 | 12/2004 | Swan et al. |
| 2005/0234370 A1 | 10/2005 | Beal et al. |
| 2008/0009815 A1* | 1/2008 | Grabenkort ............. A61M 1/81 604/74 |
| 2008/0275386 A1 | 11/2008 | Myers |
| 2014/0378946 A1 | 12/2014 | Thompson et al. |
| 2016/0095966 A1 | 4/2016 | Greener |
| 2016/0158424 A1 | 6/2016 | Chen et al. |
| 2016/0325031 A1* | 11/2016 | Miller ................. A61M 39/223 |

OTHER PUBLICATIONS

Extended European Search Report for EP Application No. 19756768.8 dated Oct. 21, 2021.

* cited by examiner

METHODS, SYSTEMS AND DEVICES FOR EXPRESSING BREASTMILK

CROSS-REFERENCE TO RELATED APPLICATIONS

This application is the National Stage of International Application No. PCT/US2019/018789 filed Feb. 20, 2019, which claims the benefit of U.S. Provisional Application No. 62/632,850 filed Feb. 20, 2018. The entirety of each of these applications is hereby incorporated by reference for all purposes.

BACKGROUND

Breast milk is known to be the best source of nutrition for a baby. Most nursing mothers utilize breastmilk expression or extracting systems because they are unable to personally feed the baby at times, for example, due to work. However, most breastmilk extracting systems, such as electric breast pumps, are generally loud, cumbersome, and indiscreet (e.g., can require removal of clothing for proper attachment and use). Therefore, many nursing mothers utilize private rooms when expressing breast milk using a breast pump. This can be inconvenient and inefficient, as well as socially stigmatizing for nursing mothers.

SUMMARY

Thus, there is need for systems, devices and methods that can provide a portable, efficient and discreet expression of breast milk.

The disclosure relates to systems, devices and methods that can efficiently express breast milk while being visually and audibly discreet, and portable.

The systems may include a breastmilk expression system for extracting milk from a breast of a female. The system may include an interface configured to deliver suction to a nipple of the breast. The system may include a breastmilk storage container configured to store breastmilk. The system may include a control device configured to be operatively (e.g., pneumatically or hydraulically) connected to the breastmilk storage container and the interface. The control device may include one or more pressure reservoirs configured to store negative pressure. The control device may be configured to cause passive suction at the interface to cause extraction of the breast milk by controlling delivery of the negative pressure stored in the one or more first pressure reservoirs from the one or more first pressure reservoirs to the interface.

In some embodiments, the control device may be operatively disposed between the interface and the breastmilk storage container.

In some embodiments, the control device may include a plurality of conduits for one or more operation pathways. In some embodiments, the control device may include a plurality of controllable valves. In some embodiments, at least one controllable valve may be disposed along each operation pathway.

In some embodiments, the plurality of conduits may include a first conduit coupled to the one or more pressure reservoirs and configured to be operatively coupled to the interface along a first operation pathway. The plurality of controllable valves may include a first controllable valve disposed along the first conduit and configured to control the delivery of the negative pressure stored in the one or more pressure reservoirs to the interface. In some embodiments, the first controllable valve may be a proportional valve.

In some embodiments, the first operation pathway may include the breastmilk storage container. The control device may be operatively disposed between the interface and the breastmilk storage container.

In some embodiments, the plurality of conduits may include a second conduit exposed to ambient air and configured to be operatively coupled to the interface along a second operation pathway. In some embodiments, the plurality of controllable valves may include a second controllable valve disposed along the second conduit and configured to provide positive pressure to the interface. In some embodiments, the second controllable valve may be a proportional valve.

In some embodiments, the plurality of conduits may include a third conduit configured to be operatively coupled to the interface and the breastmilk storage container along the first operation pathway. The plurality of controllable valves may include a third controllable valve disposed along the third conduit and configured to isolate the interface from the breastmilk storage container. In some embodiments the third controllable valve may be a pinch valve.

In some embodiments, the controller may include a processing unit and a memory. The memory may store a plurality of expression patterns. Each expression pattern may be a cyclical pattern. In some embodiments, the cyclical pattern may include a sinusoidal pattern, a waveform pattern, or any other cyclical pattern.

In some embodiments, the control device may be configured to control the plurality of controllable valves to control the delivery of the negative pressure stored in the one or more pressure reservoirs according to the one or more of the plurality of expression patterns.

In some embodiments, the system may further include a pressure conversion member operatively coupled to the one or more first pressure reservoirs and ambient air. The pressure conversion member may be configured to refill the one or more first pressure reservoirs with the negative pressure. In some embodiments, the pressure conversion member may be a pump configured to evacuate the one or more pressure reservoirs to cause the one or more pressure reservoirs to be refilled with the negative pressure. In some embodiments, the pump may be a micro-vacuum pump.

In some embodiments, the pressure conversion member may be disposed within the control device.

In some embodiments, the systems may include a system that includes an interface configured to deliver suction to a nipple of the breast. In some embodiments, the system may include a breastmilk storage container configured to store breastmilk. In some embodiments, the system may include a control device configured to be operatively coupled to the breastmilk storage container and the interface. The control device may include one or more pressure reservoirs configured to store negative pressure and a first controllable valve operatively coupled to the one or more pressure reservoirs and the interface. The control device may be configured to control the first controllable valve to control delivery of the negative pressure stored in the one or more pressure reservoirs to the interface to cause extraction of the breast milk by suction resulting from the delivery of the negative pressure.

In some embodiments, the plurality of conduits may include a first conduit coupled to the one or more pressure reservoirs and configured to be operatively coupled to the interface along a first operation pathway. The plurality of controllable valves may include the first controllable valve disposed along the first conduit and configured to control the delivery of the negative pressure stored in the one or more pressure reservoirs to the interface. The first controllable valve may be a proportional valve. The first operation pathway may include the breastmilk storage container. The control device may be operatively disposed between the interface and the breastmilk storage container.

In some embodiments, the plurality of conduits may include a second conduit exposed to ambient air and configured to be operatively coupled to the interface along a second operation pathway. In some embodiments, the plurality of controllable valves may include a second controllable valve disposed along the second conduit and configured to provide positive pressure to the interface. The second controllable valve may be a proportional valve.

In some embodiments, the plurality of conduits may include a third conduit configured to be operatively coupled to the interface and the breastmilk storage container along the first operation pathway. The plurality of controllable valves may include a third controllable valve disposed along the third conduit and configured to isolate the interface from the breastmilk storage container. In some embodiments, the third controllable valve may be a pinch valve.

In some embodiments, the controller may include a processing unit and a memory. The memory may store one or more expression patterns. Each expression pattern may be a cyclical pattern. In some embodiments, the cyclical pattern may include a sinusoidal pattern, a waveform pattern, or any other cyclical pattern. In some embodiments, the control device may be configured to control the plurality of controllable valves to control the delivery of the negative pressure stored in the one or more pressure reservoirs according to one or more of the plurality of expression patterns.

In some embodiments, the system may include a pressure conversion member operatively coupled to the one or more first pressure reservoirs and ambient air. The pressure conversion member may be configured to refill the one or more first pressure reservoirs with the negative pressure. In some embodiments, the pressure conversion member may be disposed within the control device.

In some embodiments, the methods may include a method for expression of milk from a breast. In some embodiments, the method may include providing an expression system that includes an interface, a storage device, and a control device. In some embodiments, the control device may include at least one reservoir stored with negative pressure and a first controllable valve disposed within the control device and operatively coupled to the negative pressure device. The negative pressure reservoir and the controllable valve may be operatively disposed along a first operation pathway that includes an interface engaged with a breast, a breastmilk storage container, and the control device. In some embodiments, the method may include controlling the first controllable valve to control the delivery of the negative pressure from the at least one reservoir to the interface, thereby causing suction at the interface.

In some embodiments, the first controllable valve may be controlled according to at least one expression pattern. In some embodiments, the at least one expression pattern may be a cyclical pattern. In some embodiments, the cyclical pattern may include a sinusoidal pattern, a waveform pattern, or any other cyclical pattern. In some embodiments, the at least one expression pattern may be stored by the control device.

In some embodiments, the control device may include a plurality of conduits. The plurality of conduits may include a first conduit coupled to the one or more pressure reservoirs and configured to be operatively coupled to the interface along the first operation pathway. The plurality of conduits may include a second conduit exposed to ambient air and configured to be operatively coupled to the interface along a second operation pathway. In some embodiments, the plurality of controllable valves may include a second controllable valve disposed along the second conduit.

In some embodiments, the method may include controlling the second controllable valve according to the at least one expression pattern to control an amount of suction at the interface by introducing positive pressure to the interface. In some embodiments, the first and second controllable valves may be proportional valves.

In some embodiments, the method may include disposing the interface on the breast.

In some embodiments, the negative pressure may be delivered from the control device to the interface through the plurality conduits operatively coupled to the breastmilk storage container.

In some embodiments, the control device may include one or more pressure sensors. The one or more pressure sensors may include a first pressure sensor configured to detect pressure at the interface and one or more pressure control mechanisms. The control device may be configured to control the delivery of the passive suction (negative pressure and/or positive pressure) at the interface by controlling the one or more controllable valves using the pressure.

In some embodiments, the system may further include an external pressure source configured to refill the one or more first pressure reservoirs with the negative pressure.

In some embodiments, the control device may include one or more pressure reservoirs storing positive pressure. The one or more pressure reservoirs may be configured to be refilled with the negative pressure using the one or more pressure reservoirs storing the positive pressure. In some embodiments, the pressure conversion member may be configured to convert the positive pressure stored in the one or more pressure reservoirs to the negative pressure and to refill the one or more first pressure reservoirs with the negative pressure.

In some embodiments, the system may include an adapter. In some embodiments, the adapter may include the interface and an outer housing. The outer housing may be configured to surround the interface. In some embodiments, the adapter may include a support device, such as a bra.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DESCRIPTION OF THE EMBODIMENTS

Figure 1:
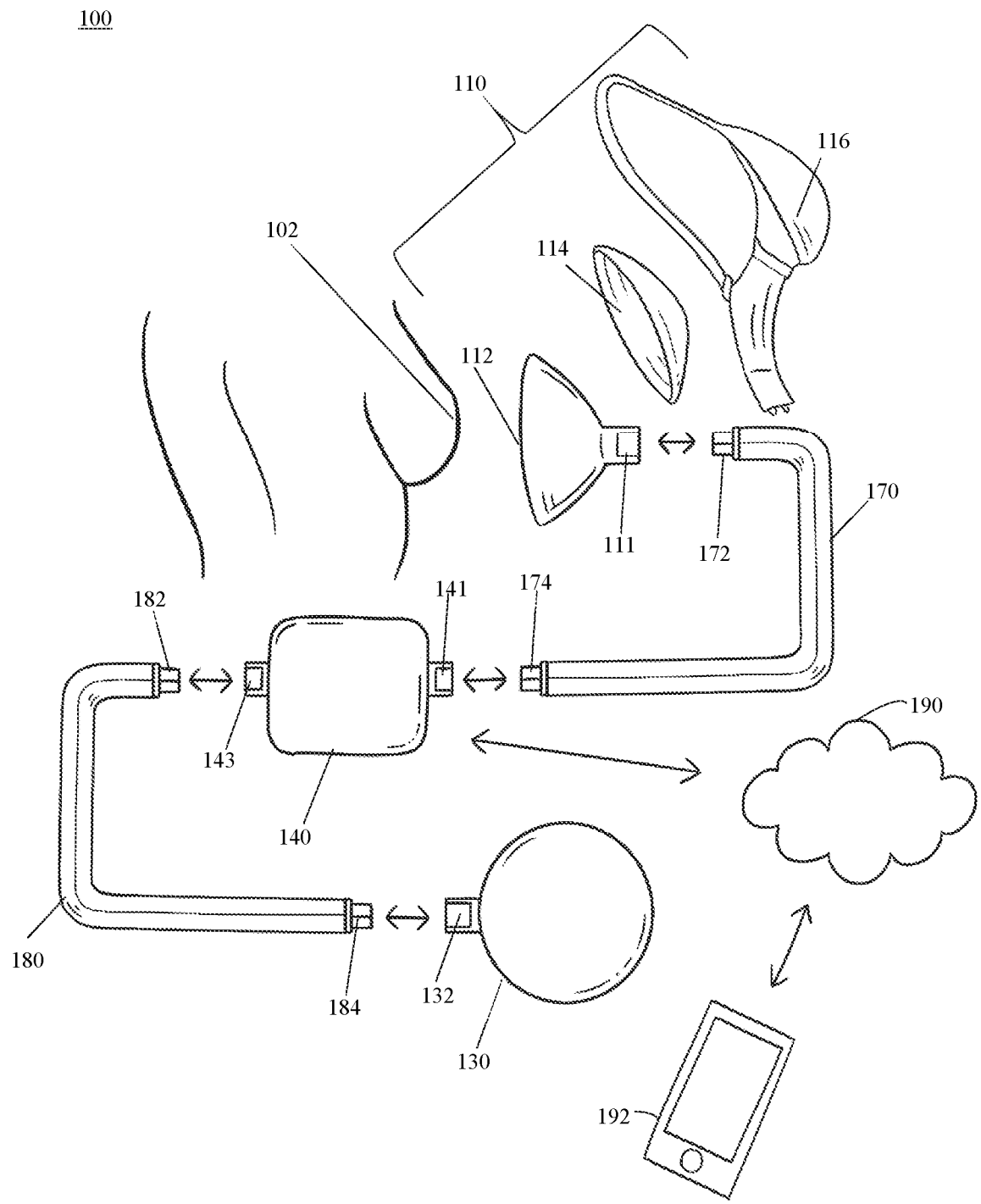
FIG. 1 shows an example of a breast expression system according to embodiments.

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The systems, devices and methods of the disclosure can discreetly and efficiently express breast milk under suction. The systems, devices, and methods are designed to passively apply suction using stored pneumatic energy (e.g., negative pressure) to achieve suction. The systems, devices, and methods does not use mechanical action to achieve suction at the breast. Therefore, by using passive energy, the suction can be substantially quiet.

Additionally, the systems, devices, and methods of the disclosure can be configured to monitor the level of expressed milk collected in the storage container. By way of example, a mobile application can be used to control and monitor the breastmilk expression. The storage container, the control device, and the breast adapter (e.g., the interface) can also be configured to be wearable. This way, the systems, devices and methods can be used in both audibly and visually discreet manners. Because the systems, devices and methods can be discrete, the wearable components can be worn by a user all day. Additionally, by placing the control device between the storage container and the breast adapter (e.g., the interface), the storage container can be easily replaced during use without disconnecting the breast adapter from the control device. The systems, devices, and methods can therefore provide a convenient, portable, and efficient expression of breast milk.

Figure 2:
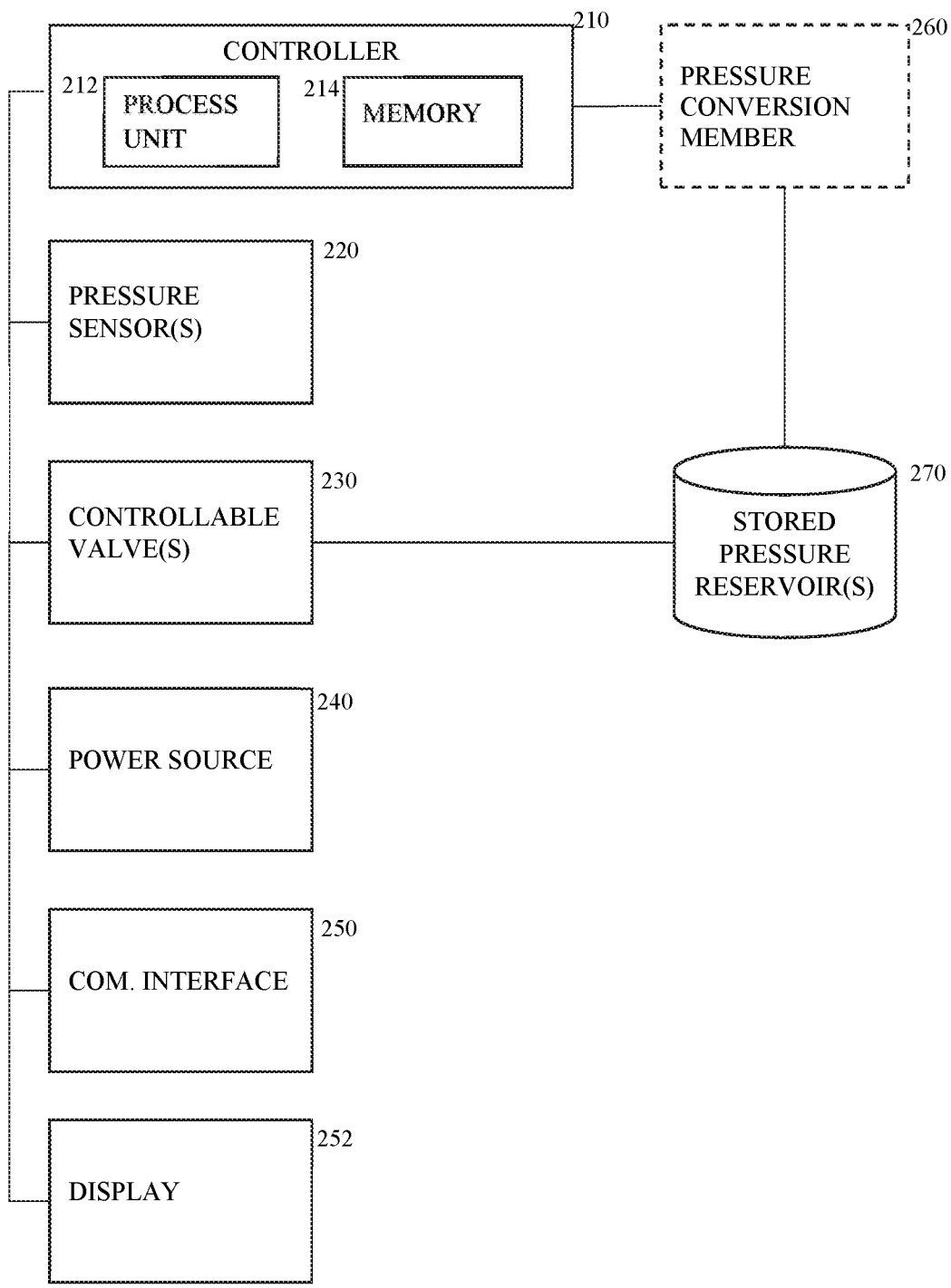
FIG. 2 shows an example of a schematic of a control device according to embodiments.
Figure 3:
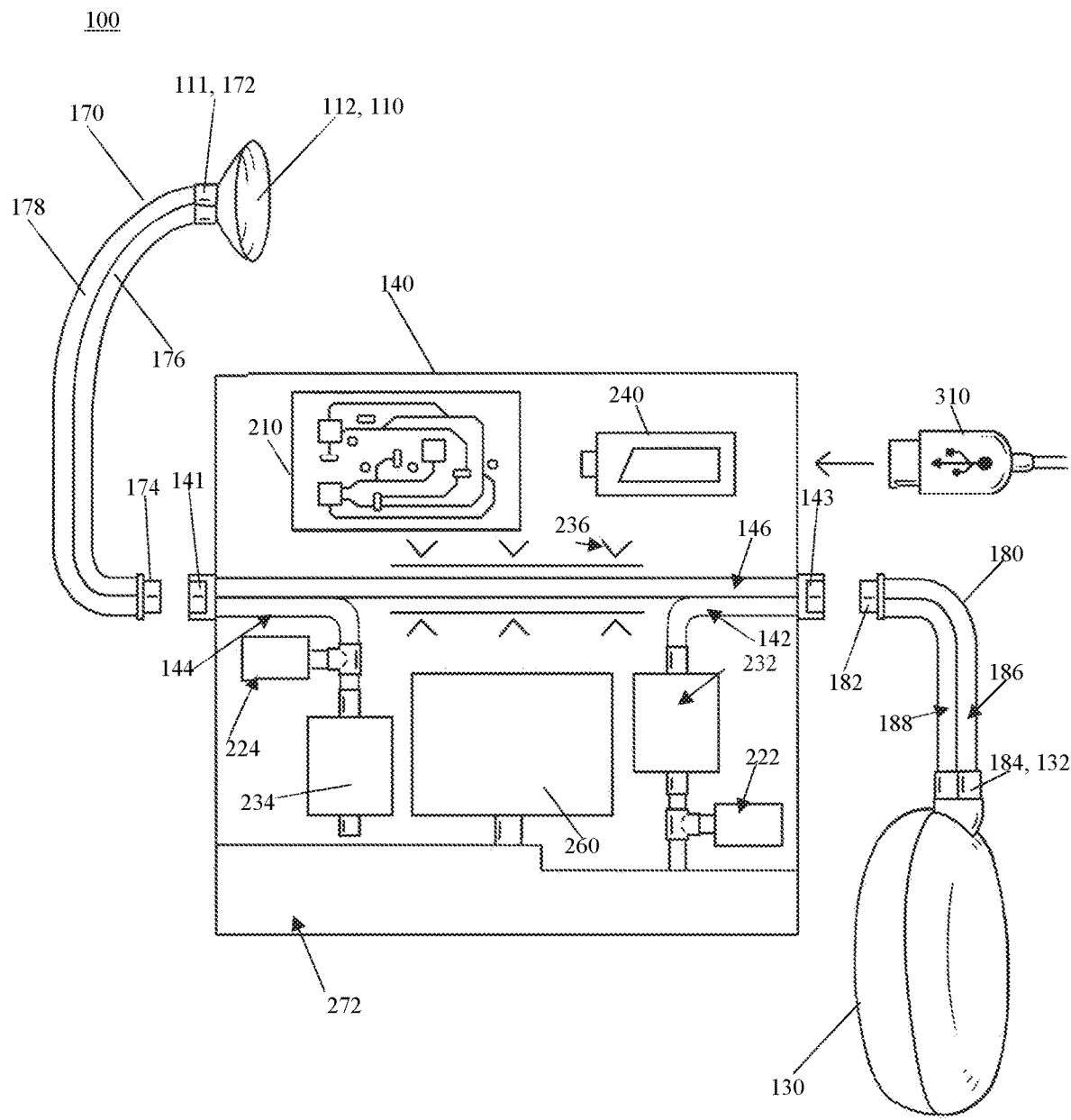
FIG. 3 shows another view of the breast expression system with a partial schematic of the control device according to embodiments.

FIGS. 1-3 show an example of a breastmilk expression system 100. In some embodiments, the system 100 may include a breast adapter (also referred to as "adapter") 110, a breastmilk storage container (also referred to as "storage container") 130, and a breastmilk expression control device (also referred to as "control device") 140.

In some embodiments, the control device 140 may be configured to provide and control the suction applied to the adapter 110 to express or extract breastmilk for collection in the storage container 130. As shown in FIGS. 1 and 3, the control device 140 may be operatively coupled to the adapter 110 by flow conduit 170 and the control device 140 may be operatively coupled to the storage container 130 by conduit member 180. Thereby, the adapter 110 may be operatively coupled to the storage container 130 via the control device 140. This way, the control device 140 is operatively disposed between the adapter 110 and the storage container 130 so that the storage container 130 can be easily replaced, as necessary, during use without disconnecting the adapter 110 from the control device 140.

In some embodiments, the adapter 110 may include an interface 112 configured to deliver suction to a nipple of a breast 102 of a female user. In some embodiments, the interface 112 may be configured to be sealed against the nipple and at least a part of the surrounding breast 102. In some embodiments, the interface 112 may be made of one or more semi-rigid materials. By way of example, the one or more materials for the interface 112 may include but is not limited to rubber, silicone, hydrogel, latex, among others, or any combination thereof.

In some embodiments, the adapter 110 may optionally include an outer housing 114 configured to enclose or surround the interface 112. In some embodiments, the outer housing 114 may be curved to compliment and/or support the breast 102. In some embodiments, the outer housing 114 may be made using any known suitable padding, such as but not limited to fabric, foam, gel, among others, etc. This way, the housing 114 may provide a smooth contour so that the interface 112/the breast adapter 110 can be discreet when worn.

In some embodiments, the interface 112 and/or the outer housing 114 may be configurable to the anatomy of the user (i.e., lactating mother (e.g., user 102)). By way of example, the interface 112 may be sized according to the breast size of the user. For example, the sizes of the interface 112 may include but are not limited to 21 mm, 24 mm, 27 mm, among others, or a combination thereof.

In some embodiments, the system 100 may optionally include a support device 116. The support device 116 may be configured to support and hold at least the interface 112 when worn. In some embodiments, the support device 116 may also be configured to support and hold the outer housing 114 so as to surround the interface 112. In some embodiments, the support device 116 may be configurable to the anatomy of the user. By way of example, the support device 116 may be customizable for size. In some embodiments, the support device 116 may be made of a material including but not limited to material(s) having moisture-wicking property, antimicrobial property, absorbent property, leak-resistant property, among others, or a combination thereof. In some embodiments, the support device 116 may be a bra, such as a convertible nursing bra.

In some embodiments, the adapter 110 may include one or more sensors (not shown) configured to measure the weight of each breast. In some embodiments, the one or more sensors may be one or more load sensors. In some embodiments, the one or more load sensors may be configured to determine a change in weight of each breast before and after a lactation cycle to determine the amount of milk delivered using the system 100 and/or by an infant during breast feeding. This can allow a user to match their milk expression to their baby's requirement; allow them to monitor calorie consumption through milk production; monitor milk production over time; correlate weight gain or loss associated with the baby against breast-milk consumed by the baby; among others; or a combination thereof. In some embodiments, the sensors may be disposed on the interface 112, the outer housing 114 and/or the support device 116.

In some embodiments, the adapter 110 may include a connection port (also referred to as "port") 111 configured to receive the flow conduit 170. In some embodiments, the connection port 111 may be disposed on the interface 112. When the flow conduit 170 is connected to the connection port 111, the interface 112/the adapter 110 may be operatively coupled to the control device 140, thereby operatively coupling the interface 112/the adapter 110 to the storage container 130 via the control device 140 and the flow conduit 180.

In some embodiments, the flow conduit (also referred to as "tubing" or "conduit") 170 and the flow conduit (also referred to as "tubing" or "conduit") 180 may include one or more tubes or capillaries. By way of example, the flow conduits 170 and/or 180 may include flexible tubing. In some embodiments, each of the flow conduits 170 and 180 may include two or more tubes or conduits. In other embodiments, the flow conduits 170 and/or 180 may include a different number of tubes or conduits (e.g., one tube/conduit, three tubes/conduits, etc.). The flow conduits 170 and/or 180 may be configured for pneumatic and/or hydraulic flow.

As shown in FIG. 3, the flow conduit 170 may include a (first) tube 176 and a (second) tube 178, in some embodiments. In some embodiments, the flow conduit 170 may include a connection port 172 and a connection port 174 disposed on opposite ends of the tubes 176 and 178. In some embodiments, the flow conduit 180 may include a (first) tube 186 and a (second) tube 188. In some embodiments, the flow conduit 180 may include a connection port 182 and a connection port 184 disposed on opposite ends of the tubes 186 and 188.

In some embodiments, the adapter 110, the flow conduit 170, the control device 140, the flow conduit 180, and/or the storage container 130 may omit one or more connection ports. By way of example, (i) the flow conduit 170 may be fixedly disposed to the interface 112/the adapter 110 and/or the control device 140 and/or (ii) the flow conduit 180 may be fixedly disposed to the control device 140 and/or the storage container 130.

In some embodiments, the storage container 130 may be configured to store and retain the milk extracted or expressed via the adapter 110/the interface 112. The storage container 130 may be configured to connect to the control device 140 via the flow conduit 180. In some embodiments, the storage container 130 may include a connection port 132 to mate with the connection port 184 of the flow conduit 180.

In some embodiments, the breastmilk storage container 130 may include an inner membrane and an outer housing that surrounds the inner membrane.

In some embodiments, the inner membrane may be a gas-permeable but not liquid-permeable so as to be porous to air particles but not breastmilk. In some embodiments, the membrane may be made of a porous flexible fabric material. In some embodiments, the inner membrane may include one or more materials including but not limited to polyethylene, polypropylene, polybuthylenterephthalat, polytetrafluorethylene, among others, or a combination thereof.

In some embodiments, the outer housing of the storage container 130 (shown in FIGS. 1 and 3) may be made of a rigid, non-collapsible material, such, as but not limited to a plastic material.

In some embodiments, the membrane and/or the breastmilk storage container 130 may be made of a different material. In some embodiments, the membrane and/or the breastmilk storage container may be reusable.

In some embodiments, the outer housing and/or the inner membrane may include one or more members to remove the breastmilk collected from the breastmilk storage container 130.

In some embodiments, the inner membrane may be configured to separate from and/or define within the outer housing so that the storage container 130 includes (i) a first area (also referred to as "reservoir area") for storing and containing the breastmilk, and (ii) a second area (also referred to as a "dry area") adjacent to and/or surrounding the first area.

In some embodiments, the control device 140 may be configured to creating suction at the interface 112 (by delivering negative pressure), by which to start and maintain the flow of milk from the breast (via the interface 112) to the storage container 130. In some embodiments, each area of the storage container 130 may be operatively coupled to a separate tube of the flow conduit 180 connected to the control device 140. In some embodiments, one tube (e.g., tube 186) may be operatively coupled to the first area and to the interface 112 via the control device 140 to collect the milk in the storage container 130 and cause suction at the interface 112. The second tube (e.g., the tube 188) may be operatively coupled to the second area so that the control device 140 may be configured to evacuate air out of the storage container 130.

By evacuating air out of the storage container 130 via the other tube (e.g., the tube 188) connected to the second area, the control device 140 may be configured to evacuate air out of the first area (i.e., the air that can pass through the membrane). By the control device 140 causing air to be evacuated through the membrane of the storage container 130 through the other tube (e.g., the tube 188), a vacuum will be left on the first area. This vacuum can result in suction at the breast interface 112 through the one tube (e.g., the tube 186) and causes milk to flow through the one tube to the storage container 130. The express milk can flow through the one tube (e.g., the tube 186) into the first area but cannot pass through the membrane and therefore is trapped and stored in the storage container 130.

Figure 4:
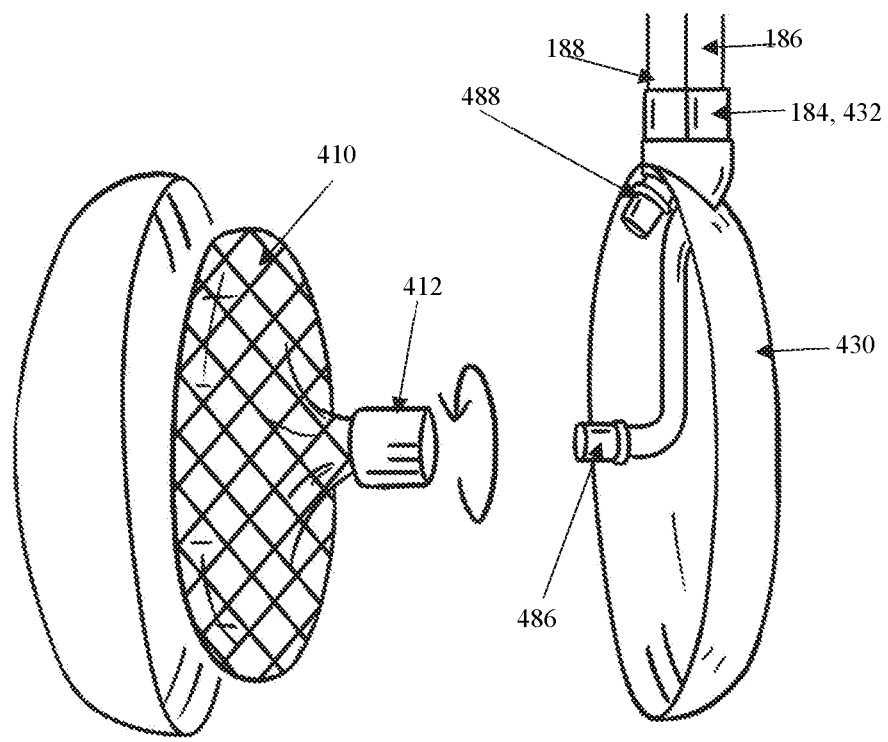
FIG. 4 shows an example of a breastmilk storage container according to embodiments.

In some embodiments, the inner membrane may be removably disposed with respect to the outer housing. The inner membrane may be included in a separate inner container and the inner container may be surrounded by the outer housing. The inner container may act as a reservoir for storing the breastmilk. FIG. 4 shows an example of a storage container 400 and is discussed in more detail below.

Figure 5:
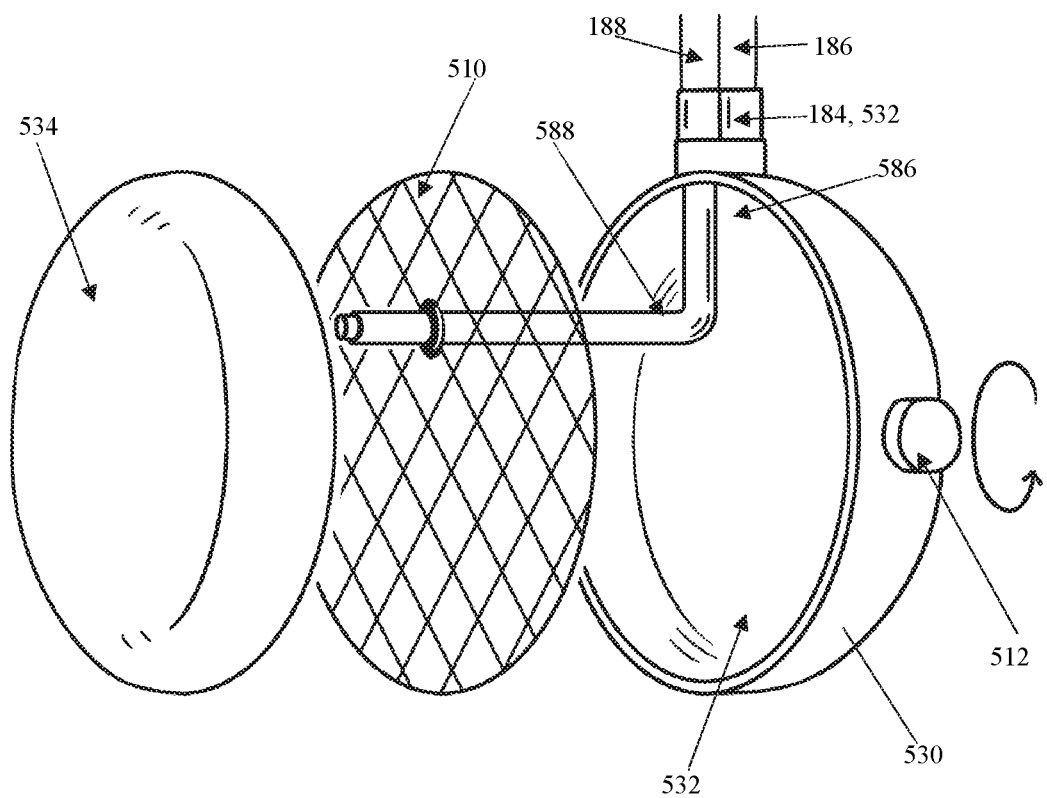
FIG. 5 shows another example of a breastmilk storage container according to embodiments.

In some embodiments, the inner membrane may be attached to the outer housing so as to divide the outer housing into the at least two areas. FIG. 5 shows an example of a storage container 500 and is discussed in more detail below.

In some embodiments, the control device 140 may be configured to control and deliver negative pressure (pneumatic energy) to the storage container 130 resulting in passive suction at the interface 112. The control device 140 may include (i) a connection port 141 configured to operatively couple the flow conduit 170 to an internal flow conduit of the control device 140 (shown in FIG. 3) and (ii) a connection port 143 to operatively couple the flow conduit 180 to an internal flow conduit of the control device 140 (shown in FIG. 3). This way, when coupled, the interface 112 may be operatively coupled to the storage container 130 via the control device 140.

In some embodiments, the control device 140 may be portable. In some embodiments, the control device 140 may be wearable. For example, the control device 140 may be provided in or may include an attachment device. For example, the attachment device may include but is not limited to a fanny pack, a clip, among others, or a combination thereof.

FIG. 2 shows a schematic of the control device 140 and FIG. 3 shows another view of the system 100 showing a partial schematic of the control device 140 for explanation purposes, according to some embodiments. In some embodiments, the control device 140 may include a controller 210 configured to control the operation of the system 100. For example, the controller 210 may be configured to control the suction applied (i.e., the negative pressure) at the interface 112, one or more pressure sensors 220, one or more controllable valve members 230 configured to adjust the suction force (i.e., rate of the negative pressure delivered) at the interface 112, one or more pressure reservoirs (or tanks) 270 configured to store pressure, and a power source 240, as shown in FIG. 2. In some embodiments, the one or more pressure reservoirs 270 may include one or more pressure reservoirs 272 (or tanks) configured to store negative pressure. In some embodiments, the one or pressure reservoirs 270 may optionally include one or more pressure reservoirs (or tanks) configured to store positive pressure.

In some embodiments the one or more pressure sensors 220 may include one or more sensors configured to determine suction force (i.e., negative pressure) applied at the interface 112, one or more sensors configured to monitor the level of pressure stored in the one or more pressure reservoirs 270, among others, or any combination thereof.

In some embodiments, the one or more controllable valves 230 may be configured to be controlled or actuated to adjust the suction force by controlling the supply of negative and/or positive pressure at the interface 112. In some embodiments, the one or more controllable valves 230 may include one or more of pneumatic valves, solenoid valves, poppet valves, diaphragm valves, piezoelectric valves, pinch valves, pneumatic solenoid valves, among others, or any combination thereof.

In some embodiments, the control device 140 may include a communication interface 250 configured to communicate data via the one or more networks 190.

In some embodiments, the controller 210 may include a processing unit 212 and a memory 214. In some embodiments, the processing unit 212 may include a microcontroller, microprocessor, among others, or any combination thereof. In some embodiments, the memory 214 may include random access memory ("RAM"), read only memory ("ROM"), EEPROM, flash memory, mass storage device, other memory technology, among others, or any combination thereof. For example, the controller 210 may be an electronic circuit board. The controller 210 may be configured to control or actuate the one or more controllable valves 230 based on the (delivered) negative pressure determined by the one or more pressure sensors 220, one or more stored patterns (e.g., stored in the memory 214), or a combination thereof. In some embodiments, the controller 210 may be configured to control the expression of the milk by controlling or actuating the one or more controllable valves 230 (e.g., by controlling at least the delivery of negative pressure from the one or more pressure reservoirs 270 storing the negative pressure) according to one or more stored patterns (also referred to as "expression pattern(s)"). This way, the one or more controllable valves 230 may be configured to control a flow of the negative pressure and the milk between the interface 112 and the storage container 130.

In some embodiments, the stored pattern(s) may have any shape or timing. For example, each of the stored pattern(s) may include one or more periods of suction (also referred to as "suction part(s))" and one or more periods of relaxation (also referred to as "relaxation part(s)"). For example, each part may have a time length and intensity (e.g., amount of suction and/or relaxation at the interface 112). In some embodiments, the stored patterns may include any number of relaxation and suction parts, length and amount (e.g., amount of relaxation and suction, respectively, at the interface 112).

In some embodiments, the controller 210 may be configured to cause the negative pressure at the interface 112 (i.e., suction force) to follow this pattern, for example, by controlling or actuating the one or more controllable valves 230 (e.g., to control at least the flow of negative pressure from the one or more pressure reservoirs 270 storing the negative pressure and/or positive pressure from ambient or atmospheric air to the interface 112). For example, the one or more stored patterns may correspond to a sucking pattern of a baby. In some embodiments, the one or more stored patterns may be personalized and specific to one or more babies of the user.

In some embodiments, the one or more stored patterns may include one or more cyclical patterns, such as sinusoidal pattern(s), waveform pattern(s), other cyclical pattern(s), or any combination thereof. In use, as this pattern of suction is applied to the nipple via the interface 112, the milk can be expected to be naturally expressed. As the negative pressure at the interface 112 causes the milk to be expressed, the milk will then flow through the conduit(s) to the storage container 130.

In some embodiments, the one or more pressure reservoirs 270 for storing negative pressure may be refillable by an internal device. For example, the control device 140 may include a pressure conversion member 260 configured to convert positive pressure to negative pressure and thereby refill the one or more pressure reservoirs 270 with negative pressure for storage. In some embodiments, the controller 210 may be configured to control the refilling or recharging of the negative pressure stored in the one or more pressure reservoirs 270 by controlling the pressure conversion member 260 to control the conversion of the positive pressure.

In some embodiments, the pressure conversion member 260 may include an actuator, such as a pump. The actuator may include but is not limited to one or more of electric diaphragm pumps, electromechanical piston pumps, pneumatic piston pumps, among others, and/or any combination thereof.

In some embodiments, the pressure conversion member 260 may be configured to evacuate the one or more pressure reservoirs 270 in order to replenish the stored negative pressure. In some embodiments, the one or more pressure reservoirs 270 may (optionally) include one or more pressure reservoirs configured to store positive pressure In some embodiments, the controller 210 may be configured to alert the user when the level of the pressure stored in the one or more pressure reservoirs 270 needs to be refilled or recharged using the one or more pressure sensors 232 monitoring the level of pressure stored in the one or more pressure reservoirs 270.

In some embodiments, the one or more pressure reservoirs 270 for storing negative pressure may be refillable or rechargeable by an external device. By way of example, an external pressure source configured to refill at least one pressure reservoir 270 with negative pressure may be a manual or electrical pump.

In some embodiments, one or more of the pressure reservoirs 270 may be configured to be removable from the control device 140. This way, one or more of the pressure reservoirs 270 may be replaced with different pressure reservoir(s) 270 having stored negative or positive pressure when a pressure reservoir is empty (i.e., no more stored negative or positive pressure, respectively).

In some embodiments, the power source 240 may be an electrical power source, such as one or more batteries. For example, the battery may include but is not limited to a camera- or watch-sized alkaline battery, lithium battery, silver-oxide battery, among others, or any combination thereof.

In some embodiments, the one or batteries may be rechargeable. In some embodiments, the power source 240 may be rechargeable through a wired connection, for example, through a USB connection 310. In some embodiments, the battery may be charged wirelessly. For example, the control device 140 may include a wireless power receiver, e.g., an integrated circuit wireless power receiver, to wirelessly receive power from a wireless power transmitter.

By using stored negative pressure, the control device 140 can cause suction at the interface 112 without any mechanical action. This can result in a substantially silent suction. Additionally, by using pneumatic energy (i.e., the stored negative pressure), the controller 140 does not require electrical energy to generate the suction. Thus, the control device 140 can last longer than conventional breast expression systems (i.e., electrical breast pumps) using the same level of power.

In some embodiments, the control device 140 may include a wired connection to a standard electrical outlet.

In some embodiments, the control device 140 may include a display 252 to display one or more operation parameters, such as, power level, vacuum pressure level, among others, or a combination thereof.

In some embodiments, the control device 140 may include a physical control interface, such as an I/O interfaces or an input/output), to allow the user to control the system 100 using one or more knobs or buttons.

In some embodiments, as shown in FIG. 1, the system 100 may be configured to communicate wirelessly to an electronic device 192 via the network 190. The electronic device 192 may be any type of electronic device capable of computation and engaging at least one or a plurality of network communications such as, for example, a television, smartphone, notebook computer (desktop, laptop, etc.), tablet, phablet, GPS (Global Positioning System) or GPS-enabled device, printer, smart watch, smart glasses, smart bracelet, wearable electronic device, PDA (personal digital assistant), pager, computing device configured for wireless communication, and/or the like.

For example, using the communication interface 250, the control device 140 may be configured to communicate and receive data with the electronic device 192 via the network 190. In some embodiments, the network 190 may be any network that can facilitate any type of data communication, such as a data network, a wireless network, a telephony network, or any combination thereof.

The electronic device 192 may include a user interface configured to display certain information and receive selections and inputs from the user. Further, the electronic device 192 can be capable of supporting a communication platform, such as a dedicated application or other type of software (referred to as an "application").

In operation, the user may interface with the application via the user interface to make selections, input data, initiate or facilitate communications with other components of the system 100, and/or perform other functions. In some embodiments, the application may include functionalities associated with recording data locally with the device 192 before, during, and/or after a breast expression session (also referred to as "expression session") for expression of breast milk with the system 100.

Each of the electronic device 192 and the control device 140 may generate or collect data or information and communicate the data or information to the other entities of the system 100 via the network(s) 190. In some embodiments, the electronic device 192 and the control device 140 may exchange operation commands via a short-range communication, thus enabling remote operation of the control device 140 by the electronic device 192. In some situations, a user may manually input data or make various selections into the electronic device 192 and/or the control device 140 (e.g., via the respective user interfaces). Each of the electronic device 192 and the control device 140 may be configured with a memory to locally store various data and information.

In some embodiments, the electronic device 192 can be capable of supporting the application that includes functionalities associated with recording data before, during, and/or after one or more expression sessions. The user or the control device 140 may be configured to communicate interactively with the application to make selections, input data, initiate or facilitate communications with other components of the system 100, and/or perform other functions via the electronic device 192. For example, the user or the control device 140 may input the volume of milk collected during a expression session; the time, date, and location of the expression session; the duration of the expression session; a frequency of use of the expression components of the system 100; performance data related to the expression components of the system 100; the suction level(s) or stored program used during the expression components of the system 100; and/or other data.

In some embodiments, the control device 140 may include a plurality of stored device settings and expression patterns (e.g., suction patterns) for one or more expression sessions, and may enable the user to select certain levels for the settings and/or stored expression patterns. For example, the user may prefer a certain goal time, a certain suction level, a certain amount of milk collected and/or other settings. In some embodiments, the electronic device 190, and/or the control device 140 may be configured with memory (e.g., persistent storage) capable of storing the set of configuration settings for the user.

In some embodiments, the system 100 may include one or more (additional) sensors. The one or more sensors may be used to measure the volume of milk collected in the storage container 130. For example, the controller 210 may determine the volume of collected milk in the storage container 130 by measuring the rate of change of negative pressure at the interface 112 using a measured value of the negative pressure in the reservoir 272 determined by the pressure sensor 224 and a fixed setting (e.g., the amount of opening which determines an amount of the negative energy delivered to the interface 112) for the first controllable valve 232.

In some embodiments, the electronic device 192 and/or the control device 140 may be configured to communicate any generated or collected data or information to a server, for example, for storage and/or further processing.

FIG. 3 shows the flow conduit 170 connected to the connection port 111 of the interface 112 and the flow conduit 180 connected to the storage container 130. The control device 140 may include a plurality of controllable valves. As shown in FIG. 3, the plurality of controllable valves may include first controllable valve 232, a second controllable valve 234, and a third controllable valve 236. In some embodiments, the first controllable valve 232 and the second controllable valve 234 may be a proportional valve, and the third controllable valve 236 may be a pinch valve. In some embodiments, the control device 140 may include less, additional and/or alternative or different controllable valves.

In some embodiments, as shown in FIG. 3, the control device 140 may include the controller 210 configured to control the plurality of controllable valves to thereby control at least the suction applied at the interface 112. In some embodiments, the control device 140 can collectively control or actuate (e.g., by opening or closing) the first controllable valve 232, the second controllable valve 234, and the third controllable valve 236 to adjust the rate of pressure delivered (i.e., the suction force) at the interface 112 from the pressure reservoir 272 storing negative pressure, for example, according to an expression pattern and/or measured value.

In some embodiments, the control device 140 may also include a first pressure sensor 222 configured to monitor the level of negative pressure stored in the one or more pressure reservoirs 272, and a second pressure sensor 224 configured to determine suction force applied at the nipple interface 112.

In some embodiments, the control device 140 may include internal flow conduits (such as tubing or capillaries) operatively coupled to the ports 141 and 143. The internal flow conduits may include one or more tubes. In some embodiments, the control device may include more tubes or conduits than shown in FIG. 3. For example, the control device 140 may include more than three tubes or conduits.

As shown in FIG. 3, the control device 140 may include a tube 142 that extends between and operatively connects to the one or more reservoirs 272 and the connection port 143. In some embodiments, the tube 142 may be operatively coupled to the tube 188 and the storage container 130 (e.g., the dry area) via the connection ports 143 and 182, respectively. In some embodiments, the control device 140 may include a tube 144 that extends between and operatively connects to the connection port 141 and atmospheric air. The tube 144 may be operatively coupled to the interface 112 and the tube 178, via the connection ports 141 and 174, respectively. In some embodiments, the control device 140 may include a tube 146 that extends between and operatively connects to the connection port 141 and the connection port 143. In some embodiments, the tube 146 may be configured to be operatively coupled to the interface 112 and the tube 176 and the storage container 130 (e.g., the reservoir area) and the tube 186 via the connection ports 174 and 182, respectively.

In some embodiments, the system 100 may include one or more operation pathways between the interface 112, the control device 140, and the storage container 130 when (i) the flow conduit 170 is operatively coupled to the interface 112 and the control device 140 and (ii) the flow conduit 180 is operatively coupled to the control device 140 and the storage container 130. In some embodiments, the operation pathways can provide a closed-loop pneumatic system that can continuously provide suction using stored negative pressure/negative energy.

By way of example, when connected, (i) the interface 112, the tubes 142, 146, 176, 186 and 188, the controllable valves 232 and 236, the pressure sensor 222, the control device 140, and the storage container 130 may define a first operation pathway; and (ii) the interface 112, the tubes 144 and 178, the pressure sensor 224, the control device 140, and the second controllable valve 234 may define a second operation path. The first operation path may be used to control the amount of suction at the interface 112; and the second operation path may be used to control the amount of relaxation at the interface 112 and can ensure that milk is transported away from the breast. It will be understood that the system 100 may include more or less operation pathways.

By way of example, after the adapter 110 is properly positioned and connected to the control device 140 and the storage container 130 is connected to the control device 140, the control device 140 may be operated. The starting state of an expression session can be that there is no suction applied at the interface 112. When the expression session is initiated, the controller 210 can cause passive suction at the interface 112 for breast expression by delivering the stored negative pressure from the negative pressure reservoir 272 using the first operation pathway. The controller 210 may cause the first controllable valve 232 disposed along the tube 142 and operatively disposed between the negative pressure reservoir 272 and the breast interface 112 via the storage container 130 to open. As the first controllable valve 232 opens, a correspondingly increasing flow of air can naturally occur between the breast interface 112 and the negative pressure reservoir 272 via the storage container 130. This can result in air flowing from the breast interface 112 via the tubes 176 and 146 into the negative pressure reservoir 272 via the tubes 188 and 142 and the storage container 130 (e.g., the dry area), and thus creating a suction at the breast interface 112 (via tubes 146 and 176). By opening or closing the first controllable valve 232 by different amounts, the controller 210 can adjust automatically the amount of airflow from the breast interface 112 via the first operation path, and thus control the suction that is being created at the breast. For example, the controller 210 can control the intensity and duration of the suction pattern of an expression session by adjusting the airflow from the breast interface 112 through the first controllable valve 232.

In some embodiments, the tube 144 may be operationally coupled to the second controllable valve 234 (e.g., through the second controllable valve 234) to the surrounding atmosphere (e.g., ambient air), and the interface 112 via the tube 178. The second controllable valve 234 may be controlled by the controller 210 to adjust (by degree) the amount of airflow from the surrounding atmosphere (e.g. ambient air to introduce positive pressure) into the breast interface 112 and adjust the rate of relaxation at the interface 112. By suppling airflow to the breast interface 112 via the tube 178, transport of milk back towards the breast via the tube 176 can also be prevented and can ensure that milk can be transported away from the interface 112 (and breast 102) and towards the storage container 130.

In some embodiments, the controller 140 may be configured to implement a proportional-integral-derivative (PID) algorithm provided in one or more programs stored in the controller 212 so as to minimize error(s) in pressure so that the pressure at the interface 112 can be maintained at the intended level of suction. In some embodiments, the stored program (e.g., using PID algorithm) can determine the amount by which the first controllable valve 232 is opened.

In some embodiments, according to the PID algorithm based on the stored program, if the controller 210 determines that the actual pressure exceeds the intended pressure, the controller 210 can cause (i) the first pressure controllable valve 232 to close to prevent any further flow of air from the interface 112 to the pressure reservoir 272 and (ii) the second controllable valve 234 to open to release ambient or atmospheric air (e.g., positive pressure) into the interface 112 in order to reduce the suction pressure back to the intended value. By this combined action of the two proportional valves, any errors (i.e., differences between intended pressure and actual pressure at the interface 112) can be kept at a minimum and the suction force at the nipple can follow a programmed pattern.

In some embodiments, the tube 146 may be configured to pass through the third controllable valve 236 so as to provide a means whereby the controller 210 can isolate the breast interface 112 from the breastmilk storage container 130 during the relaxation part of the expression pattern (e.g., when the controllable valves 232 and 236 are closed). This can ensure that the relaxation in suction, e.g., during an expression session, can occur only at the interface 112 and not within the overall system. This way, the overall system (which includes the milk storage vessel) can then remain under peak suction until the next suction part of an expression pattern. This can also greatly reduce the amount of suction energy that may be needed during an expression session. Additionally, by isolating the interface 112 from the storage container 130 by the control device 140 and the third controllable valve 236 (e.g., when the first controllable valve 232 and the third controllable valve 236 are closed), the system can ensure that milk can (when necessary) be actively prevented from flowing towards the interface 112, including during the relaxation part of an expression pattern when there can be a risk of fluid leakage.

During the suction part of an expression pattern, there can be generally a minimal risk of leakage because the vacuum via the tube 176 can help to maintain a seal between the breast 102 and the interface 112 but this seal can be vulnerable during the relaxation part of an expression pattern. In some embodiments, at the end of each suction part (during the relaxation part) of an expression pattern, the controller 210 can be programmed to take action to allow airflow through the tube 176 to the breast interface 112 by opening the first controllable valve 232 in order to ensure that all milk is evacuated from the breast interface 112 and the tube 146 at least as far as the third controllable valve 236 in order to greatly minimize if not eliminate any risk of milk leakage at the breast interface 112. This can prevent a user from experiencing physically and/or socially discomfort.

Also, by locating the third controllable valve 236 within the control device 140 and the control device 140 between the interface 112 and the storage container 130, the storage container 130 may be easily and conveniently removed for another milk storage container without disturbing the flow conduit 170 between the interface 112 and the control device 140. In some embodiments, the tube 186 may be connected to the reservoir area of the storage container 130 defined by the membrane and the tube 188 may be connected to the dry area of the storage container 130. This way, the milk may be collected within and confined to the reservoir area of the storage container 130.

This way, the control device 140 via the operation pathways can control a flow or rate of the negative pressure and/or the milk, for example, according to an expression pattern, between the interface 112 and the storage container 130, for example, by controlling or actuating the controllable valves (e.g., controllable valves 232, 234, and 236).

In some embodiments, the control device 140 may include the pressure conversion member 260 that may be configured to refill the pressure reservoir 272. As shown in FIG. 3, the pressure conversion device 260 may be disposed to or attached to the control device 140. In some embodiments, the controller 210 may be configured to activate the pressure conversion member 260 based on the pressure sensed by the pressure sensor 222 (e.g., measure value of pressure) or based on the breastmilk expression pattern. This may be considered a third operation pathway. Over time, as the expression session progresses, more and more ambient or atmospheric air may enter the pressure reservoir 272 from the interface 112 via the storage container 130 (e.g., the dry area) and the tubes 188 and 142. The addition of this air may cause the reservoir 272 to become depleted of negative pressure. The controller 210 may cause the pressure conversion member 260 to be activated until the level of negative pressure (i.e., level of vacuum) in the negative pressure reservoir is restored.

In some embodiments, the control device 140 may activate the pressure conversion member 260 to correspond to the rate at which the negative pressure (i.e., vacuum) is being depleted by the expression session. In this example, the pumping mechanism can be continuously active and can reduce the noticeable noise as compared to a repetitive stop-start activation.

When the expression session is completed and/or the user wishes to remove the expressed milk and/or the container 130 (e.g., for storage and/or usage), the user may instruct the system 100 via the control device 140 to do a "purge" of the tubes 176, 146 and 180. By way of the example, when instructed to do a "purge," the controller 210 may cause the first and second controllable valves 232 and 234 to open and to thereby create a high flow of air through the tubes 176, 146 and 180. This airflow can result in substantially no suction at the interface 112, therefore no further milk expression will take place during the "purge," but the airflow through the tubes 176, 146, and 180 will transport all residual milk from this operation pathway into the storage container 130 (e.g., the reservoir area). After the "purge," the breastmilk storage container 130 may be disconnected without any concern that residual milk will drip from the conduits (e.g., tubes 176, 146 and/or 180) and create a spill. The breastmilk may then be ready for removal from the disconnected breastmilk storage container.

FIGS. 4 and 5 show examples of breastmilk storage containers 400 and 500, respectively. Like the storage container 130, both of the storage containers 400 and 500 include a connection port connection 184 that is configured to be connected to the flow conduit 180 (the tubes 186 and 188).

As shown in FIG. 4, the storage container 400 may include an inner container 410 surrounded by a removable outer housing 430 and a connection port 432 disposed on the outer housing 430. In some embodiments, the storage container 400 may include a flow conduit connected to the connection port 432. The flow conduit may include tubes 486 and 488.

In this example, the inner container 410 may include a membrane on one or more surfaces. As discussed above, membrane may be a gas-permeable but not liquid-permeable so as to be porous to air particles but not breastmilk. In some embodiments, the membrane may be made of a porous flexible fabric material. In some embodiments, the inner membrane may include one or more materials including but not limited to polyethylene, polypropylene, polybuthylenterephthalat, polytetrafluorethylene, among others, or a combination thereof.

In some embodiments, the inner container 410 may include a one-way valve embedded in a removable cap 412. The cap 412 may be a screw-cap, flip-cap, or any cap that can be fitted to the bag. The cap (and one-way valve) 412 may be configured to operatively connect to the tube 486, which is operatively coupled to the tube 186 via the port 184. This way, when connected and the system is operating, the milk may be delivered to and retained in the inner container 412 via the one-way valve. In this example, to remove the milk, the outer housing 430 maybe opened and the inner container 410 may be removed. The milk may then be removed by opening the cap 412. In this example, the storage container 400 (the inner container 410 and the removable outer housing 430) and/or the inner container 410 may be switched out during operation.

Like the storage container 130, the storage container 400 may include a reservoir area and a dry area. The inner container 410 may be considered the reservoir area. The area defined by outer housing 430 surrounding the inner container 410 may be considered the dry area. In some embodiments, the tube 188 may be operatively coupled to the tube 488 via the connection ports 184 and 132 to operatively communicate with the dry area of the storage container 400.

In some embodiments, the membrane may be fixedly attached to a side of the outer housing. FIG. 5 shows an exploded and open view of the storage container 500. In this example, the storage container 500 may include a membrane 510 fixedly disposed to a side of an outer housing 530. As discussed above, membrane may be a gas-permeable but not liquid-permeable so as to be porous to air particles but not breastmilk. In some embodiments, the membrane may be made of a porous flexible fabric material. In some embodiments, the inner membrane may include one or more materials including but not limited to polyethylene, polypropylene, polybuthylenterephthalat, polytetrafluorethylene, among others, or a combination thereof.

In this example, the membrane 510 may be fixed to side 532 of the outer housing 530. Like the storage container 130, the storage container 500 may include a reservoir area and a dry area. The area defined by the membrane 510 and the side 532 may be considered to be the reservoir area described with respect to the storage container 130. The area defined by opposing side 534 and adjacent to the membrane 510 may be considered the dry area of the storage container 500.

Like the storage container 130, the dry area may be operatively coupled to the tube 188 via the connection ports 184 and 532 and tube 588. The reservoir area may be operatively coupled to the tube 186 via the connection ports 184 and 532 and the tube 586 (not illustrated). In some embodiments, the storage container 500 may include a cap 512 disposed on the side 532. The cap 512 may be a screw-cap, flip-cap, or any cap that can be fitted to the storage container 500. The milk collected in the reservoir area of the storage container 500 may then be removed by opening the cap 512. In this example, the storage container 500 may be switched out during operation, for example, by disconnecting the conduit 180 from the storage container 500 and replacing with another storage container.

In some embodiments, one or more of the components of the system may be reusable. For example, the conduits or tubes (e.g., 170, 180, etc.), the adapter (e.g., interface 112), and/or the breastmilk storage container (e.g., 130) may be removable from the control device for replacement of different parts, such as breastmilk storage container, as well as be cleaned and/or sterilized for additional uses.

Figure 6:
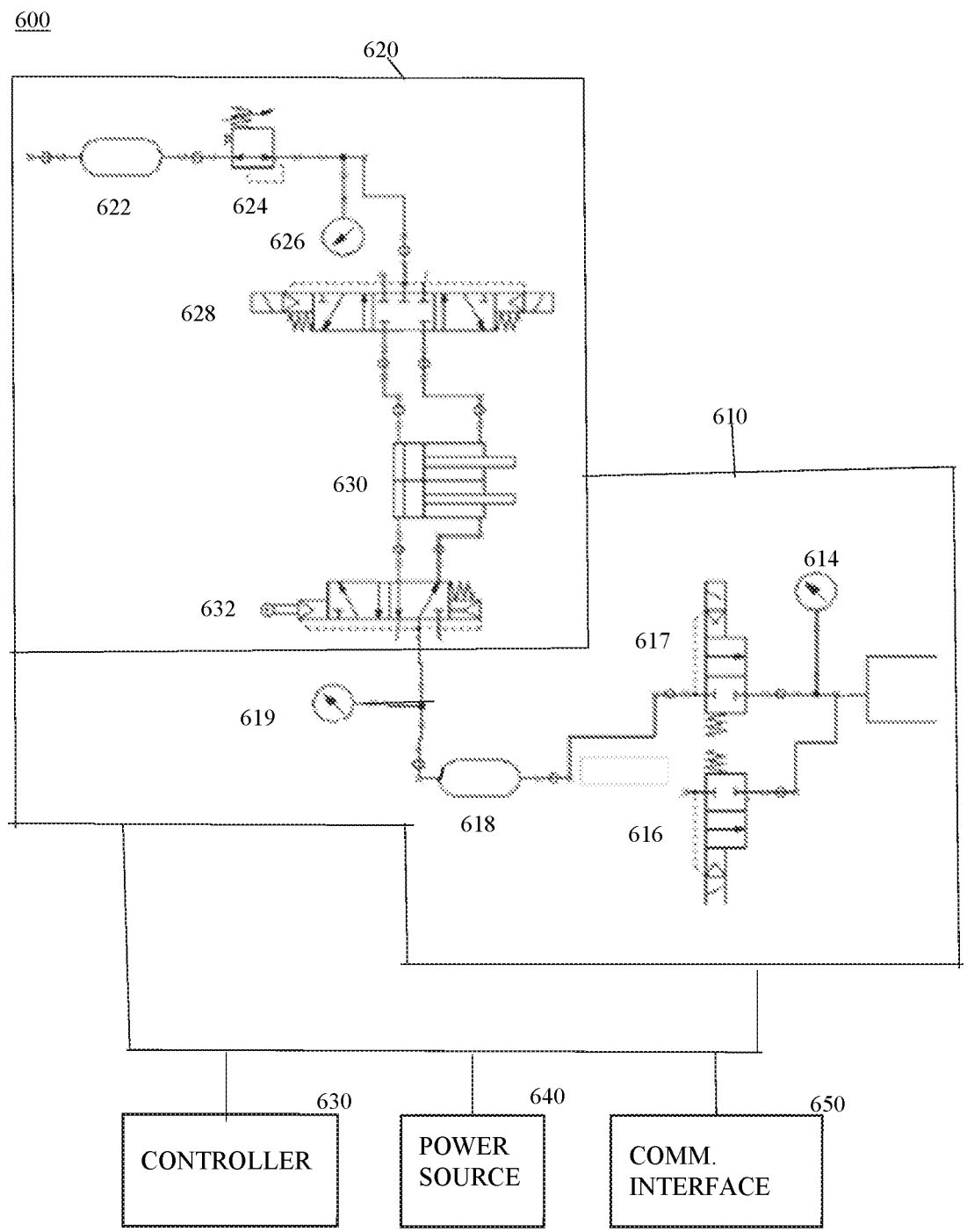
FIG. 6 shows an example of a schematic of another control device according to embodiments.

FIG. 6 shows another example of a control device 600 configured to refill one or more pressure reservoirs with negative pressure by converting stored positive pressure. The control device may be configured to be attached to the interface 112 and the storage container 130 using the flow conduits 170 and 180, shown in FIG. 1.

In some embodiments, the control device 600 may include a suction member (or negative pressure member) 610, a pressure conversion member (or positive pressure member) 620 connected to the suction member 610 via tubing, a controller 640, a power source 650, and a communication interface 649. In this example, the controller 640, the power source 650 and the communication interface 649 may correspond to the controller 210, the power source 240 and the communication interface 250, shown in FIG. 2, respectively. The components of the suction member 610 and the pressure conversion member 620 may be connected, for example, using conduits.

In some embodiments, the suction member (or negative pressure member) 610 may include one or more pressure sensors 614 configured to determine suction force applied at the nipple interface 112, a controllable valve 616 and a controllable valve 617 configured to adjust the rate of pressure delivered (i.e., the suction force) at the interface 112, a (first) pressure reservoir 618 configured to store negative pressure, and one or more pressure sensors 619 (disposed at the pressure reservoir 618) configured to monitor the level of negative pressure stored in the pressure reservoir 618.

In some embodiments, the pressure conversion member 620 may include a (second) pressure reservoir (or pressure tank) 622 configured to refillably store positive pressure, a first valve 624 (e.g., a control valve/pressure regulator) configured to control the output of positive pressure from the pressure reservoir 622, and a pressure sensor 626 configured to detect the monitor the level of positive pressure stored in the pressure reservoir 622. In this example, the pressure conversion mechanisms may include a (second) valve (e.g., solenoid valve manifold) 628, a piston arrangement (e.g., two-way piston) disposed in cylinder chambers 630, and a (third) valve 632 (e.g., a proportional solenoid valve). In some embodiments, the piston arrangement 630 may include at least two (separate) cylinder that in which the pistons are disposed. Each cylinder may include two chambers disposed on opposite sides of the piston disposed in that cylinder. In this example, the controller 640 may be configured to control the pressure conversion member 620 to control the refilling or recharging of the first pressure reservoir 618 with negative pressure converted from the positive pressure stored in the second pressure reservoir 622 based on the pressure levels in the reservoir 618 determined by the sensor 619.

In use, when the sensor 619 determines that the pressure reservoir 618 needs to be refilled, the controller 642 can cause the (first) valve 624 to open to allow positive pressure from the second pressure reservoir 62 to be available to the input port disposed at the valve 628. When the switch valve 628 is opened, the positive pressure is delivered to one of the input ports of the piston arrangement (cylinder) 630. The delivery of the positive pressure to one of the cylinders 630 can cause the driving piston in that cylinder 630 to move under the pneumatic force of the positive pressure. The direction of the driving piston can depend on which cylinder (via the input port) that is opened. As the driving piston moves, negative pressure can be created in the other cylinder on the opposite side of the piston from the direction of movement (of the piston). When the driving piston has reached the end of the cylinder, the valve 628 may be closed to hold the pressure in the cylinder and hold the piston in the cylinder in position. The valve 624 may also be closed to preserve the positive pressure stored in the pressure reservoir 622. The valve 632 may be opened (i.e., moved to an open position away from the default position) to allow the negative pressure to create a pressure gradient between the valve port and the reservoir 618. The pressure gradient can evacuate air from the pressure reservoir 618, thereby increasing the level of negative pressure in the pressure reservoir 618. The valve 632 may be closed (i.e., moved back to the default position) so that the negative pressure may be stored in the reservoir 618.

If the pressure sensor 619 detects that the negative pressure stored in the pressure reservoir 618 is low, the controller 640 can cause the process above to repeated using the opposite input port of cylinder 630. This way, the driving piston can be forced in the opposite direction back to its starting position. The act of resetting the driving piston can in and of itself achieve further evacuation of the negative pressure reservoir.

Once there is sufficient negative pressure in the negative pressure reservoir it can then be deployed as described previously to deliver an appropriate suction waveform at the nipple interface Although FIG. 6 shows one reservoir for the positive pressure reservoir 622 and the negative pressure reservoir 618, it will be understood that there may be more than one reservoir for the positive pressure reservoir 622 and/or the negative pressure reservoir 618.

In some embodiments, the pressure conversion member 620 may replace the pressure conversion member 260 of the control device 140 shown in FIG. 3.

The conversion of positive pressure to negative pressure and the suction resulting from the air pressure does not use an electric motor or electric pump. Thus, the conversion of the positive pressure to negative pressure and the resulting suction can be substantially silent.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. A breast expression system for extracting milk from a breast of a female, the system comprising:
    an interface configured to deliver suction to a nipple of the breast;
    a breastmilk storage container configured to store breastmilk; and
    a control device configured to be operatively coupled to the breastmilk storage container and the interface, the control device including one or more pressure reservoirs configured to store negative pressure;
    wherein:
    the control device is operatively disposed between the interface and the breastmilk storage container;
    the control device is configured to cause passive suction at the interface to cause extraction of the breast milk by controlling delivery of the negative pressure stored in the one or more pressure reservoirs to the interface;
    the control device includes a plurality of conduits for one or more operation pathways;
    the control device includes a plurality of controllable valves;
    at least one controllable valve is disposed along each operation pathway;
    the plurality of conduits includes a first conduit coupled to the one or more pressure reservoirs and configured to be operatively coupled to the interface along a first operation pathway;
    the plurality of controllable valves includes a first controllable valve being disposed along the first conduit and configured to control the delivery of the negative pressure stored in the one or more pressure reservoirs to the interface;
    the first controllable valve is a proportional valve;
    the first operation pathway includes the breastmilk storage container;
    the plurality of conduits includes a breastmilk conduit configured to be operatively coupled to the interface and the breastmilk storage container along the first operation pathway;
    the plurality of controllable valves includes a second controllable valve being disposed along the breastmilk conduit and configured to isolate the interface from the breastmilk storage container; and
    the second controllable valve is a pinch valve.

2. The system according to claim 1, wherein:
    the plurality of conduits includes an ambient air conduit exposed to ambient air and configured to be operatively coupled to the interface along a second operation pathway;
    the plurality of controllable valves includes a third controllable valve being disposed along the ambient air conduit and configured to provide positive pressure to the interface; and
    the third controllable valve is a proportional valve.

3. The system according to claim 1, wherein:
    the control device includes a processing unit and a memory, the memory storing a plurality of expression patterns,
    each expression pattern is a cyclical pattern; and
    the control device is configured to control the plurality of controllable valves to control the delivery of the negative pressure stored in the one or more pressure reservoirs according to one or more of the plurality of expression patterns.

4. The system according to claim 1, further comprising:
    a pressure conversion member operatively coupled to the one or more pressure reservoirs and ambient air,
    the pressure conversion member being configured to refill the one or more pressure reservoirs with the negative pressure.

5. The system according to claim 4, wherein the pressure conversion member is disposed within the control device.

6. A breast expression system for extracting milk from a breast of a female, the system comprising:
    an interface configured to deliver suction to a nipple of the breast;
    a breastmilk storage container configured to store breastmilk; and
    a control device configured to be operatively coupled to the breastmilk storage container and the interface;
    the control device including one or more pressure reservoirs configured to store negative pressure and a plurality of controllable valves, the plurality of controllable values includes a first controllable valve operatively coupled to the one or more pressure reservoirs and the interface;
    wherein:
    the control device is configured to control the first controllable valve to control delivery of the negative pressure stored in the one or more pressure reservoirs to the interface to cause extraction of the breast milk by suction resulting from the delivery of the negative pressure;

the control device includes a plurality of conduits for one or more operation pathways;

the plurality of conduits includes an ambient air conduit exposed to ambient air and configured to be operatively coupled to the interface along a second operation pathway;

the plurality of controllable valves includes a second controllable valve being disposed along the ambient air conduit and configured to provide positive pressure to the interface; and the second controllable valve is a proportional valve;

the plurality of conduits includes a breastmilk conduit configured to be operatively coupled to the interface and the breastmilk storage container along a first operation pathway;

the plurality of controllable valves includes a third controllable valve being disposed along the breastmilk conduit and configured to isolate the interface from the breastmilk storage container; and the third controllable valve is a pinch valve.

7. The system according to claim 6, wherein:

the plurality of conduits includes a first conduit coupled to the one or more pressure reservoirs and configured to be operatively coupled to the interface along the first operation pathway;

the first controllable valve being is disposed along the first conduit and configured to control the delivery of the negative pressure stored in the one or more pressure reservoirs to the interface;

the first controllable valve is a proportional valve; and the first operation pathway includes the breastmilk storage container, the control device being operatively disposed between the interface and the breastmilk storage container.

8. The system according to claim 6, wherein:

the control device includes a processing unit and a memory, the memory storing a plurality of expression patterns, each expression pattern is a cyclical pattern; and the control device is configured to control the plurality of controllable valves to control the delivery of the negative pressure stored in the one or more pressure reservoirs according to one or more of the plurality of expression patterns.

9. The system according to claim 6, further comprising:

a pressure conversion member operatively coupled to the one or more pressure reservoirs and ambient air, the pressure conversion member being configured to refill the one or more pressure reservoirs with the negative pressure;

wherein the pressure conversion member is disposed within the control device.

10. A method for expression of milk from a breast, the method comprising:

providing an expression system that includes an interface, a storage device, and a control device;

the control device including at least one reservoir stored with negative pressure and a plurality of controllable valves, the plurality of controllable values includes a first controllable valve disposed within the control device and operatively coupled to the storage device, the at least one reservoir and the first controllable valve being operatively disposed along a first operation pathway that includes the interface engaged with a breast, the storage device, and the control device; and controlling the first controllable valve to control the delivery of the negative pressure from the at least one reservoir to the interface, thereby causing suction at the interface;

wherein:

the control device includes a plurality of conduits;

the plurality of conduits includes a first conduit coupled to the at least one reservoir and configured to be operatively coupled to the interface along the first operation pathway;

the plurality of conduits includes a second conduit exposed to ambient air and configured to be operatively coupled to the interface along a second operation pathway;

the plurality of controllable valves includes a second controllable valve being disposed along the second conduit, the second controllable valve is a proportional valve;

the plurality of conduits includes a third conduit configured to be operatively coupled to the interface and the storage device along the first operation pathway;

the plurality of controllable valves includes a third controllable valve being disposed along the third conduit and configured to isolate the interface from the breastmilk storage container; and the third controllable valve is a pinch valve.

11. The method according to claim 10, wherein the first controllable valve is controlled according to at least one expression pattern, each expression pattern being a cyclical pattern.

12. The method according to claim 11, the method further comprising:

controlling the second controllable valve according to the at least one expression pattern to control an amount of suction at the interface by introducing positive pressure to the interface, wherein the first controllable valve is a proportional valve.

13. The method according to claim 12, wherein:

the negative pressure is delivered from the control device to the interface through the plurality of conduits operatively coupled to the storage device.

* * * * *